(12) United States Patent
Joseph et al.

(10) Patent No.: US 12,318,250 B2
(45) Date of Patent: *Jun. 3, 2025

(54) METHOD AND DEVICE FOR TRACING THE MOTION OF BLOOD VESSEL BOUNDARIES

(71) Applicants: Healthcare Technology Innovation Centre, Chennai (IN); Indian Institute of Technology Madras (IIT Madras), Chennai (IN)

(72) Inventors: Jayaraj Joseph, Chennai (IN); Raj Kiran Vangapandu, Chennai (IN); Nabeel Pilaparambil Mashood, Chennai (IN); Mohanasankar Sivaprakasam, Chennai (IN)

(73) Assignees: HEALTHCARE TECHNOLOGY INNOVATION CENTRE, Chennai (IN); INDIAN INSTITUTE OF TECHNOLOGY MADRAS (IIT MADRAS), Chennai (IN)

( * ) Notice: Subject to any disclaimer, the term of this patent is extended or adjusted under 35 U.S.C. 154(b) by 365 days.

This patent is subject to a terminal disclaimer.

(21) Appl. No.: 17/996,506

(22) PCT Filed: Apr. 27, 2021

(86) PCT No.: PCT/IN2021/050412
§ 371 (c)(1),
(2) Date: Oct. 19, 2022

(87) PCT Pub. No.: WO2021/220301
PCT Pub. Date: Nov. 4, 2021

(65) Prior Publication Data
US 2023/0200773 A1  Jun. 29, 2023

(51) Int. Cl.
*A61B 8/08* (2006.01)
*A61B 8/00* (2006.01)

(52) U.S. Cl.
CPC ............ *A61B 8/0891* (2013.01); *A61B 8/486* (2013.01); *A61B 8/5207* (2013.01)

(58) Field of Classification Search
CPC ...... A61B 8/0891; A61B 8/486; A61B 8/5207
See application file for complete search history.

(56) References Cited

U.S. PATENT DOCUMENTS

| 8,313,437 | B1 * | 11/2012 | Suri | A61B 8/0891 600/443 |
|---|---|---|---|---|
| 2005/0249391 | A1 * | 11/2005 | Kimmel | G06T 7/143 382/128 |
| 2011/0299753 | A1 * | 12/2011 | Suri | G06T 7/0012 382/131 |
| 2012/0259224 | A1 * | 10/2012 | Wu | G16H 50/30 600/443 |
| 2020/0151872 | A1 * | 5/2020 | Ma | A61B 8/085 |
| 2020/0286227 | A1 * | 9/2020 | Corredor | A61B 1/000096 |
| 2023/0210497 | A1 * | 7/2023 | Joseph | A61B 8/0891 600/437 |

* cited by examiner

*Primary Examiner* — Baisakhi Roy (57) ABSTRACT

Embodiments of the present disclosure are directed to an vascular-dynamics-monitoring device (100) and methods for tracing a motion of boundaries of a vessel in a human body. The method features an automated gating of vessel walls' echoes in an ultrasound frame input to the vessel, accurate shift estimation for the gated vessel wall region, despite the presence of echoes from moving structures adjacent to the vessel and real-time trace of vessel walls' boundaries.

20 Claims, 6 Drawing Sheets

METHOD AND DEVICE FOR TRACING THE MOTION OF BLOOD VESSEL BOUNDARIES

PRIORITY DETAILS

The present application is based on, and claims priority from International Application PCT/IN2021/050412 filed 27 Apr. 2021 and Indian Application Number 202041017855 filed on 27 Apr. 2020, the disclosures of which are hereby incorporated by reference herein.

TECHNICAL FIELD

The present disclosure relates to medical monitoring and analysis, and more particularly to tracing motion of blood vessel boundaries.

BACKGROUND

Arterial lumen diameter and wall thickness (assessed as intima-media thickness) constitute important sub-clinical measurements of cardiovascular risks. Several multicentre clinical studies and meta-data analyses have provided outcomes that recommend these measures as established surrogates and independent markers of various cardiovascular events, pathologies, and disease progression. Simultaneous measurement of their instantaneous values can help furnish several functional and material properties of the blood vessels. These properties include the distensibility (or compliance), stiffness index, modulus of elasticity, local pulse wave velocity and its variation within a cardiac cycle, viscoelasticity, wall-buffering function, endothelial dysfunction, central blood pressure, etc.

The non-invasive measurement of arterial diameter or wall thickness and their changes is performed using imaging technologies traditionally. This involves two tasks, the first of which is a localization or identification of vessel wall echoes which is a high-level task and the second is tracking those locations over time in each new scan. These task of manually inspecting each scanned frame and tracking the boundary locations is tedious and time consuming, and thereby need further attention.

While a method's accuracy is implicit, it is desirable if the measurements are yielded real-time and in automated or semi-automated fashion. Such methods that depend minimally on the operator are likely to reduce the time consumed for the measurement procedure and contribute towards better repeatability. This is particularly important to accelerate large scale studies or field-level screening, and also in settings with resource-constraints. Recent works have reviewed several automated and semi-automated techniques that employ segmentation on B-mode ultrasound images to evaluate the diameter and wall thickness. These state-of-the-art B-mode techniques meet the necessary clinical standards and requirements concerning the measurement of the artery's dimensional parameters. However, these modalities are expensive, and the advanced features required for performing such measurements are not augmented to the entry-level devices. Additionally, they are non-scalable, demand a skilled operator, and do not cater to out-of-clinic applications. In the context of India, the legal constraints imposed by the Pre-Natal Diagnostic Techniques (PNDT) act restrict imaging ultrasound devices to be deployed to field, unless otherwise with special approvals. This has affected the ready availability of these ultrasound technologies to the rural sector of India where the resources are scarce, both in terms of man-power and machinery.

Measurement of change in diameter is done based on determining a motion of vessel boundaries in addition to determining the boundary walls. There remains a need to provide for accurate determinations of the motion of vessel boundaries.

In light of the above, there is a need to overcome the above stated disadvantages.

SUMMARY

Embodiments of the present disclosure are directed to a system and methods for tracing a motion of a vessel in a human body. The method features an automated gating of vessel walls' echoes in an ultrasound frame input to the vessel, accurate shift estimation for the gated vessel wall region, despite the presence of echoes from moving structures adjacent to the vessel and real-time trace of vessel walls' boundaries.

Embodiments of the present disclosure are directed to a method for tracing motion of blood vessel boundaries in a human body. The method includes receiving, by an vascular-dynamics-monitoring device, a plurality of ultrasound signals from the blood vessel, continuously extracting, by the vascular-dynamics-monitoring device, at least two consecutive ultrasound frames from the plurality of ultrasound signals received, identifying, by an vascular-dynamics-monitoring device, locations of a proximal wall and a distal wall of the blood vessel based on the at least two consecutive ultrasound frames by the, vascular-dynamics-monitoring device; dynamically extracting, by the vascular-dynamics-monitoring device, at least one echo region of proximal wall and at least one echo region of distal wall from each of the at least two ultrasound frames based on the identified locations of the proximal wall and distal wall of the blood vessel, comparing, by the vascular-dynamics-monitoring device, the at least one echo region of proximal wall and at least one echo region of distal wall from each of the at least two consecutive ultrasound frames to determine at least one delay waveform between the each of the regions or first time-derivative of unwrapped analytic phase waveforms of the each of the proximal wall echo region and the distal wall region of each of the at least two consecutive ultrasound frames, continuously determining, by the vascular-dynamics-monitoring device, at least one extremum of the delay waveform or at least two extrema of interest of the first time-derivative of the unwrapped analytic phase waveforms, wherein the at least one extremum of the delay waveform or the average shift in the at least two extrema of interest of the first time-derivative of the unwrapped analytic phase waveforms is indicative of a shift of the at least one echo region on each of the proximal wall and the distal wall, and tracing, by the vascular-dynamics-monitoring device, the motion of the proximal wall and the distal wall based on the continuously determined motion shift of the at least one echo region on each of the proximal wall and the distal wall.

Another embodiment of the present disclosure is directed to continuing tracing of the proximal wall and the distal wall until the tracing concurs with an expected motion of the proximal wall and the distal wall.

Another embodiment of the present disclosure is directed to an ultrasound frame being a digitized data frame of the ultrasound echo signal with a finite number of samples.

Another embodiment of the present disclosure is directed to the proximal wall and the distal wall of the blood vessel of the subject moving in opposite directions.

Another embodiment of the present disclosure is directed to wherein dynamically identifying at least one echo region on each of the proximal wall and the distal wall comprises placing at least two windows with dynamically allocated sizes around each of the plurality of ultrasound signals received from the identified proximal wall and the identified distal wall.

Another embodiment of the present disclosure is directed to comparing samples of the at least one echo region of each of the proximal wall and the distal wall of each of the at least two consecutive ultrasound frames to determine a delay waveform between the corresponding echo regions of the at least two consecutive ultrasound frames comprises comparing samples of the echo regions to determine an alignment dissimilarity between the echo regions, generating a two dimensional alignment error matrix based on the alignment dissimilarity between the echo regions, translating the two dimensional error matrix to an accumulated distance matrix, determining local minimum accumulated errors and global minimum accumulated errors from the accumulated distance matrix, and generating the delay waveform based on the determined local minimum accumulated errors and the global minimum accumulated errors.

Another embodiment of the present disclosure is directed to processing samples of the at least one echo region of each of the proximal wall and the distal wall of each of the at least two consecutive ultrasound frames to determine a first derivative of unwrapped phase change waveform between the at least two consecutive ultrasound frames comprises determining a quadrature phase counterpart corresponding to each of the at least one echo region of each of the at least two ultrasound frames by applying Hilbert transform on the each of the at least two ultrasound frames, generating a single sideband (SSB) signal corresponding to each of the at least one echo region of each of the at least two ultrasound frames by adding the each of the echo regions to the corresponding quadrature phase counterpart, constructing continuous phase waveforms of each of the echo regions by performing a tangent inverse operation on the SSB signal corresponding to each of the at least two ultrasound frames, constructing the unwrapped phase waveforms by performing a time-domain unwrapping operation, differentiating the unwrapped phase waveforms of each of the at least one echo region of each of the proximal wall and the distal wall with respect to time once.

Another embodiment of the present disclosure is directed to the echo regions including an equal number of samples.

Another embodiment of the present disclosure is directed to the echo regions including an unequal number of samples.

Embodiments of the present disclosure are directed to vascular-dynamics-monitoring device for identifying boundaries of a blood vessel in a human body. The vascular-dynamics-monitoring device includes a memory storing ultrasound frames, a signal transceiver configured for receiving a plurality of ultrasound echo signals from a proximal wall and a distal wall of the blood vessel, a sample extractor and a controller that is communicatively connected to the sample extractor, the signal transceiver and the memory. The sample extractor is configured for continuously extracting at least two consecutive ultrasound frames from the plurality of ultrasound echo signals received from the at least one echo region, dynamically extracting at least one echo region from each of the at least two ultrasound frames, and storing the at least two consecutive ultrasound frames in the memory. The controller is configured for comparing, by the vascular-dynamics-monitoring device, the at least one echo region from each of the at least two consecutive ultrasound frames to determine at least one delay waveform between the each of the regions or first time-derivative of unwrapped analytic phase waveforms of the each of the proximal wall echo region and the distal wall region of each of the at least two consecutive ultrasound frames, continuously determining, by the vascular-dynamics-monitoring device, at least one extremum of the delay waveform or at least two extrema of interest of the first time-derivative of the Unwrapped analytic phase waveforms, wherein the at least one extremum of the delay waveform or the average shift in the at least two extrema of interest of the first time-derivative of the unwrapped analytic phase waveforms is indicative of a shift of the at least one echo region on each of the proximal wall and the distal wall, and tracing, by the vascular-dynamics-monitoring device, the motion of the proximal wall and the distal wall based on the continuously determined motion shift of the at least one echo region on each of the proximal wall and the distal wall.

BRIEF DESCRIPTION OF FIGURES

Having thus described the disclosure in general terms, reference will now be made to the accompanying figures, wherein:

It should be noted that the accompanying figures are intended to present illustrations of exemplary embodiments of the present disclosure. These figures are not intended to limit the scope of the present disclosure. It should also be noted that accompanying figures are not necessarily drawn to scale.

DETAILED DESCRIPTION OF EMBODIMENT

Various embodiments of the present disclosure will now be described in detail with reference to the accompanying drawings. In the following description, specific details such as detailed configuration and components are merely provided to assist the overall understanding of these embodiments of the present disclosure. Therefore, it should be apparent to those skilled in the art that various changes and modifications of the embodiments described herein can be made without departing from the scope and spirit of the present disclosure. In addition, descriptions of well-known functions and constructions are omitted for clarity and conciseness.

Also, the various embodiments described herein are not necessarily mutually exclusive, as some embodiments can be combined with one or more other embodiments to form new embodiments. Herein, the term "or" as used herein, refers to a non-exclusive or, unless otherwise indicated. The examples used herein are intended merely to facilitate an understanding of ways in which the embodiments herein can be practiced and to further enable those skilled in the art to practice the embodiments herein. Accordingly, the examples should not be construed as limiting the scope of the embodiments herein. Further it should be possible to combine the flows specified in different figures to derive a new flow.

As is traditional in the field, embodiments may be described and illustrated in terms of blocks which carry out a described function or functions. These blocks, which may be referred to herein as managers, engines, controllers, units or modules or the like, are physically implemented by analog and/or digital circuits such as logic gates, integrated circuits, microprocessors, microcontrollers, memory circuits, passive electronic components, active electronic components, optical components, hardwired circuits and the like, and may optionally be driven by firmware and software. The circuits may, for example, be embodied in one or more semiconductor chips, or on substrate supports such as printed circuit boards and the like. The circuits constituting a block may be implemented by dedicated hardware, or by a processor (e.g., one or more programmed microprocessors and associated circuitry), or by a combination of dedicated hardware to perform some functions of the block and a processor to perform other functions of the block. Each block of the embodiments may be physically separated into two or more interacting and discrete blocks without departing from the scope of the disclosure. Likewise, the blocks of the embodiments may be physically combined into more complex blocks without departing from the scope of the disclosure.

The embodiments herein and the various features and advantageous details thereof are explained more fully with reference to the non-limiting embodiments that are illustrated in the accompanying drawings and detailed in the following description.

The embodiments disclosed herein can be implemented through at least one software program running on at least one hardware device and performing network management functions to control the elements. The elements shown in FIGS. 1-6 include blocks which can be at least one of a hardware device, or a combination of hardware device and software module.

In accordance with embodiments disclosed herein, document management involves acquiring any document and then retrieving document properties to map them to a pre-stored set of documents. Depending upon the document category, relevance of data inside document in any form such as text, QR code, etc. can be determined for providing services to the subject.

Reference in this specification to "one embodiment" or "an embodiment" means that a particular feature, structure, or characteristic described in connection with the embodiment is included in at least one embodiment of the present technology. The appearance of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described, which may be requirements for some embodiments but no other embodiments.

Moreover, although the following description contains many specifics for the purposes of illustration, anyone skilled in the art will appreciate that many variations and/or alterations to said details are within the scope of the present technology. Similarly, although many of the features of the present technology are described in terms of each other, or in conjunction with each other, one skilled in the art will appreciate that many of these features can be provided independently of other features. Accordingly, this description of the present technology is set forth without any loss of generality to, and without imposing limitations upon, the present technology.

Figure 1:
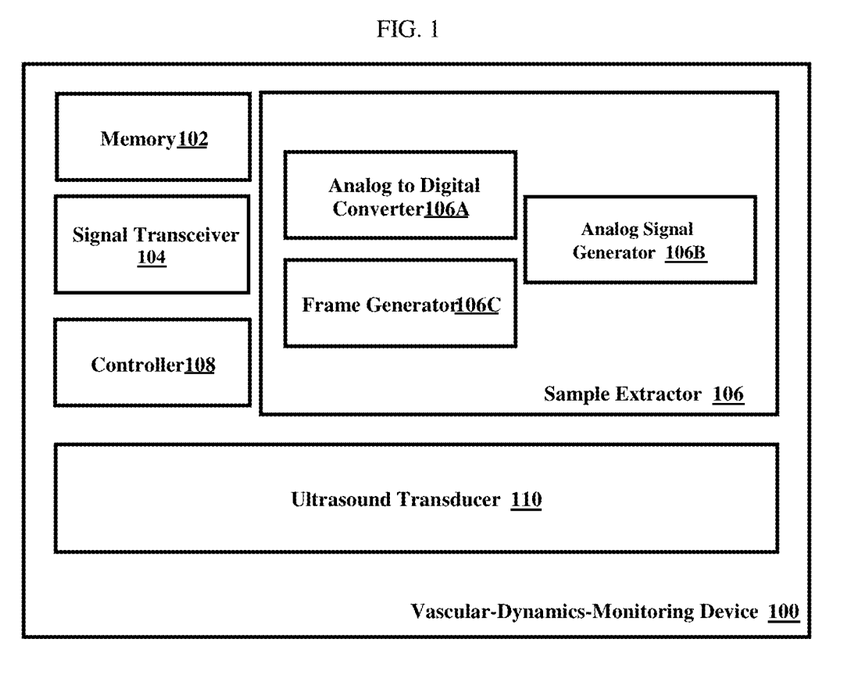
FIG. 1 illustrates a vascular-dynamics-monitoring device for tracing motion of boundaries of a vessel in a body, in accordance with various embodiments of the present disclosure.

FIG. 1 illustrates a vascular-dynamics-monitoring device 100 for tracing the motion of a blood vessel. The vascular-dynamics-monitoring device 100 includes a memory 102, a signal transceiver 104, a sample extractor 106 and an ultrasound transducer 110 and a controller 108. The ultrasound transducer 110 may include an inbuilt (or external) transmitter and a receiver that transmit and receive ultrasound signals. While the generated ultrasound signal of the ultrasound transducer 110 propagates through a target site on a body, several ultrasound echoes are generated from various structures in the transmission path. These echoes are captured by the signal transceiver 104 and is converted into signature analog waves using an analog signal generator 106B of the sample extractor 106. These analog signals are then processed with various signal conditioning elements, as desired using the frame generator 106C. These conditioned ultrasound analog signals are converted into digital signals using an analog to digital converter 106A and are stored temporarily in the memory 102. It is a continuous process and is controlled by the controller 108. The digitised ultrasound echo signals are transferred to a digital domain for further analyses and to perform various measurements by implementing aforesaid methods. Of note, an echo signal with a finite number of samples in the digital domain henceforth referred to as an ultrasound frame.

The ultrasound frames, acquired via the sample extractor 106, contain echoes formed from various tissue interfaces along the axis of the ultrasound scan. If the target artery vessel is situated along the scan line, the echoes formed from the boundaries of the artery appear to be shifting in each consecutive frame with a characteristic pattern. Typically, in the case of arteries, such boundaries can be named as proximal wall and distal wall of the artery. The proximal and distal walls would be moving in a direction opposite to each other. In the following paragraphs, two systematic methods, a time domain method and a frequency domain method, are described to locate and identify boundaries of the artery (viz. proximal wall and distal wall of the artery) by analysing the acquired ultrasound echo frames. It should be noted that, although the following method described in the context of an artery, is directly applicable to any vascular structure encompassing fluid with a characteristic motion.

In some embodiments, the vascular-dynamics-monitoring device 100 may include communication units pertaining to communication with remote computers, servers or remote databases over a communication network. The communication network can include a data network such as, but not restricted to, the Internet, local area network (LAN), wide area network (WAN), metropolitan area network (MAN) etc. In certain embodiments, the communication network can include a wireless network, such as, but not restricted to, a cellular network and may employ various technologies including enhanced data rates for global evolution (EDGE), general packet radio service (GPRS), global system for mobile communications (GSM), Internet protocol multimedia subsystem (IMS), universal mobile telecommunications system (UMTS) etc.

The controller 108 can be, but not restricted to, a Central Processing Unit (CPU), a microprocessor, or a microcontroller. The controller 108 executes sets of instructions stored on the memory 102.

The memory 102 includes storage locations to be addressable through the controller 108. The memory 102 is not limited to a volatile memory and/or a non-volatile memory. Further, the memory 102 can include one or more computer-readable storage media. The memory 102 can include non-volatile storage elements. For example, non-volatile storage elements can include magnetic hard discs, optical discs, floppy discs, flash memories, or forms of electrically programmable memories (EPROM) or electrically erasable and programmable (EEPROM) memories. In some embodiments, the memory 102 is communicably coupled to third party storage, cloud storage and the like.

The ultrasound frames acquired via the signal transceiver (104) contain echoes formed from various tissue interfaces along the axis of the ultrasound scan. If the target artery vessel is situated along the scan line, the echoes formed from the boundaries of the artery appear to be shifting in each consecutive frame with a characteristic pattern. Typically, in the case of arteries, such boundaries can be named as proximal wall and distal wall of the artery. The proximal and distal walls would be moving in a direction opposite to each other. In the following paragraphs, a systematic method is described to locate and identify boundaries of the artery (viz. proximal wall and distal wall of the artery) by analysing the acquired ultrasound echo frames. It should be noted that, although the following method described in the context of an artery, is directly applicable to any vascular structure encompassing fluid with a characteristic motion.

Figure 2:
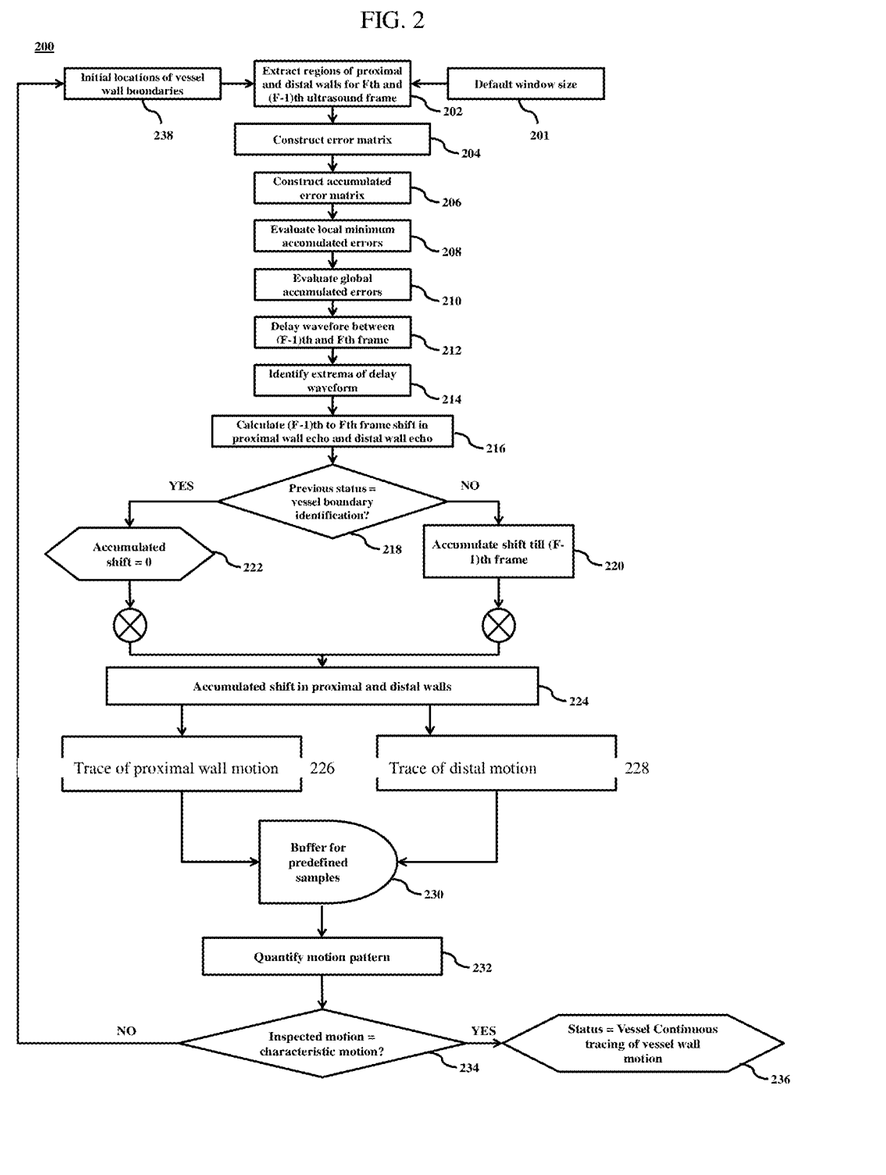
FIG. 2 is flow diagram illustrating a time domain method for tracing motion of boundaries of a vessel in a human body, in accordance with various embodiments of the present disclosure.

FIG. 2 illustrates a time domain method (200) for tracing motion of boundaries of a vessel in the human body, in accordance with various embodiments of the present disclosure. In the method disclosed herein, as described in FIG. 2, continuous tracing of a dynamic location and motion pattern of the vessel boundaries is described. It is achieved by analysing a relative motion of the identified boundaries across the continuous ultrasound frames. Although the following sections are described in the context of an arterial vessel and tracing its proximal and distal walls, the method is directly applicable to any vascular structure encompassing fluid with a characteristic motion.

Once approximate locations of vessel boundaries are identified with a suitable manual or automated method, the approximate locations of vessel boundaries act as the initial locations of the proximal and distal walls (step 238). Two windows of sufficient and equal size (dynamically allocated) are placed around the echoes originated from the proximal and distal wall boundaries (step 201 and step 202). The centre portion of the said windows are placed, however not constrained, at the previously identified boundary locations. Such extracted subsets from $F^{th}$ and $(F-1)^{th}$ frames are then analysed.

The alignment dissimilarity between the extracted proximal wall's subset of $F^{th}$ and $(F-1)^{th}$ frames is measured by generating an error matrix E(k,n).

In an embodiment, ultrasound frames are continuously collected and stored in a buffer. Two consecutive frames, the current frame F and its previous frame (F−1) are used at a time. Typically, both $F^{th}$ and $(F-1)^{th}$ frame have an equal number of samples (N), else are made equal. From these the proximal and the distal wall subsets are extracted. Then the alignment dissimilarity between these frames' subsets is measured by generating an error matrix. Since two consecutive frames are used, the error matrix will be a two-dimensional matrix. The same operation can be performed with any desired number of successive frames, which would result in an error matrix with the corresponding dimensionality (step 204).

Any $n^{th}$ column in the two-dimensional error matrix E(k,n) is populated by comparing a sample at index n in $F^{th}$ frame subset, with (2K+1) samples in $(F-1)^{th}$ frame subset, extracted using a window with its centre at the $n^{th}$ index of the frame (F−1) subset. It can be compared in any form such as, but not limited to, algebraic or logical. For example, the samples are compared using an 'absolute difference operator' in Equation (1) and the description that follows. This comparison operation is performed for all the samples in the $F^{th}$ frame subset ($S_1$ signal) by correspondingly shifting the window centre in the $(F-1)^{th}$ frame subset ($S_2$ signal). Subsequently, there are N columns in error matrix E(k,n) with each column consisting of (2K+1) samples. Here, k represents the lags from the selected windows' centre index in $(F-1)^{th}$ frame subset from which the samples are extracted for comparison against one sample extracted from the $F^{th}$ frame subset. In each column of E(k,n) the indices of minima represent the lags that align the samples in $F^{th}$ frame subset with the samples in $(F-1)^{th}$ frame subset.

$$E(k,n)=|S_1(n)-S_2(n-k)|; n=[1,N] \text{ and } k=[-K,K] \quad (1)$$

Once the error matrix E(k,n) is derived, it is translated to an 'accumulated error matrix' D(k,n) as a representation of the cumulative errors while traversing across the length of the frame via a various lag path (step 206). However not constrained to, the first column of D(k,n) is initialized as the first column of E(k,n) as:

$$D(k,1)=E(k,1). \quad (2)$$

From the second column to the $N^{th}$, elements of D(k,n) in a $k^{th}$ row and $n^{th}$ column are obtained by adding the element in E(k,n) corresponding to the $k^{th}$ row and $n^{th}$ column with the smallest of the elements extracted from $(k-1)^{th}$, $k^{th}$ and $(k+1)^{th}$ rows in the $(n-1)^{th}$ column, as shown in Equation (3):

$$D(k,n) = E(k,n) + \min\begin{cases} D(k-1, n-1) \\ D(k, n-1), n=2, 3, \ldots N \\ D(k+1, n-1) \end{cases} \quad (3)$$

This form of generating accumulated error matrix process iteratively adds the minimum of the adjoining elements presents one column apart. Now the 'local minimum accumulated errors' are computed by traversing in the reverse direction, that is from $N^{th}$ column to Pt column of D(k,n).

These accumulated error matrices are used to derive the delay waveform L(n), in the form of lags that best align the consecutive frame signals, for the proximal and distal wall echo regions. The procedure of construction of L(n) involves, however not constrained, initialising the lag corresponding to the minimum of the last column elements in D(k,n) as L(N);

$$L(N)=\arg(\min D(k,N)), \forall k. \quad (4)$$

The other elements of the matrix L(n) are to be estimated for n=N−1 to 1. For this, the elements from any column n corresponding to lags L(n+1)−1, L(n+1) and L(n+1)+1 are collected, and the lag corresponding to the minimum of these elements is assigned to L(n), as give below.

$$L(n)=\arg(\min D(k,n)), \text{ for, } k \in [L(n+1)+1, L(n+1), L(n+1)-1] \text{ and } n=N-1, N-2, \ldots 1 \quad (5)$$

Therefore, the sub-paths yielding local minimum accumulated errors (step 208) when sequentially connected, it constructs the complete path estimating L(n) and producing a 'global minimum accumulated error' (step 210).

For more robust evaluation of delay waveform L(n), a modified D(k,n) matrix construction can also be adopted. In this approach, instead of constructing D(k,n) for all the columns (n=1: N), it is constructed for columns that are spaced m positions apart. Therefore, the constructed accumulated error matrix' D(k,i), where i=1: m: N, consists of only N/m columns. Here, the first column of D(k,i) is initialised as the first column of E(k,n). Further, for the columns (i=2: N/m), any element of D(k,i) in row k and column i is evaluated by first identifying (2m+1) paths that connect the element of E(k,n) in row k and column i*m to the elements in column (i−1)*m and rows (k−m): (k+m). These elements in E(k,n) along the individual paths are added to obtain (2m+1) such path summations and the minimum of these summation values corresponding to a particular path is added to the element of E(k,n) in the $k^{th}$ row and $(i*m)^{th}$ column. This value is assigned to the element of D(k,i) in the $k^{th}$ row and $i^{th}$ column.

Now once the delay waveforms are generated as alluded above (step 212), for both the proximal and distal wall region, the extrema of their respective delay waveforms are identified and labelled (step 214). Extrema of the delay waveform represent the shifts of the proximal and distal subset echoes from $(F-1)^{th}$ to $F^{th}$ frame. The shifts of proximal and distal walls corresponding to the $F^{th}$ frame are added to their accumulated shifts (resultant shift till $(F-1)^{th}$ frame) (step 216). Note that, if the tracing has just started, this previously accumulated shift can be set to a predefined value (typically initialized with zero). This procedure, therefore, continuously traces the shifts in the echoes of the selected region with every new incoming frame. The exact locations of the vessel wall boundaries in the current frame are computed by adding the current accumulated shifts with the initially identified wall locations (step 220 and step 222). These exact locations further assist in shifting of the window centre that extracts the proximal and distal wall regions in the consecutive frames (step 226 and step 228). The proximal wall and distal wall locations are buffered for sufficient samples (step 230), and the mutual motion pattern between them is quantified (step 232). This motion pattern is inspected by comparing the expected physiological characteristic motion pattern of the arterial walls (step 234). The tracing of the walls is continued until the inspected motion concurs with the expected characteristic motion; otherwise, the locations of the walls are again freshly identified (step 238).

Figure 3:
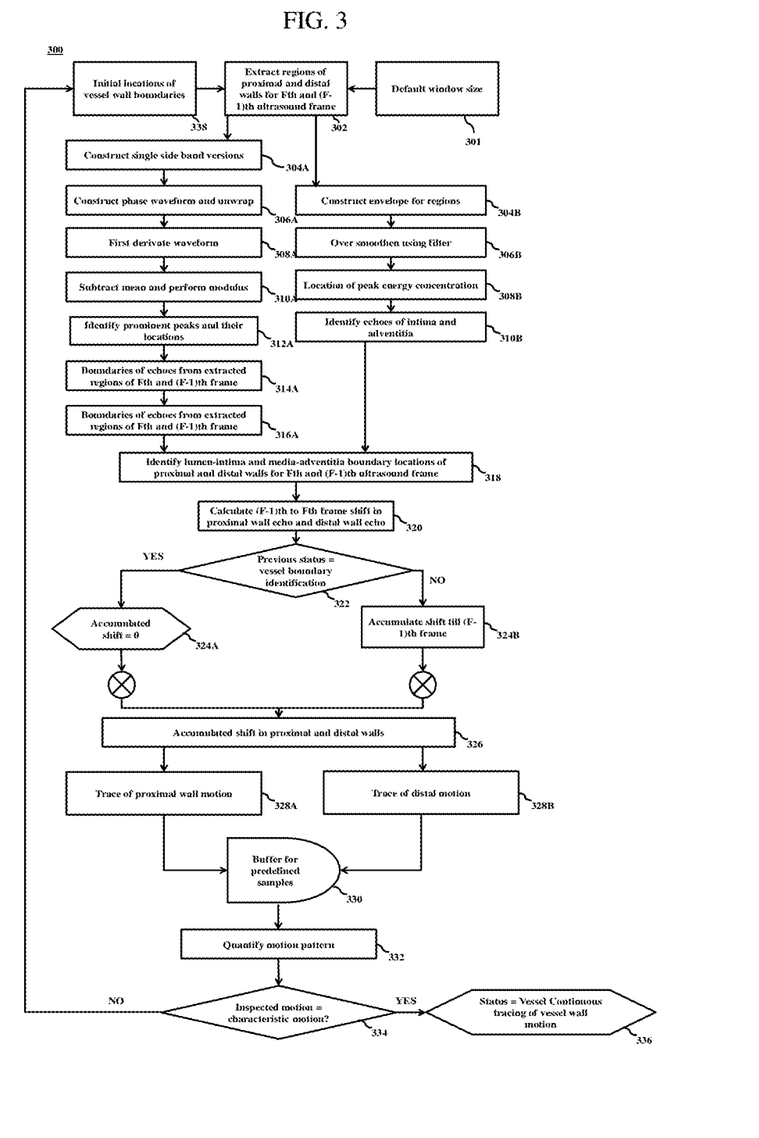
FIG. 3 is a flow diagram illustrating a frequency domain method for tracing motion of boundaries of a vessel in the human body, in accordance with various embodiments of the present disclosure.

FIG. 3 illustrates an independent frequency domain method for tracing motion of boundaries of a vessel in a human body, in accordance with various embodiments of the present disclosure. The locations of vessel wall boundaries (proximal and distal wall locations) identified via a suitable manual or automated method act as the initial reference locations to trace the wall dynamics and motion (or vibrations) of vessel walls. Initially, a window with the dynamically allocated size is used to extract the proximal and distal wall echo regions constituting a sufficient number of samples (step 301 and step 302). Hilbert transform operation is applied on these proximal and distal wall echo regions of the $F^{th}$ and $(F-1)^{th}$ frame which yields their respective quadrature-phase counterpart. By adding the regions from the original frames (F and (F−1)) with their quadrature versions, G and (G−1), respectively single-sideband (SSB) signals are generated (step 304A). Phase waveforms of these regions are now evaluated using the constructed single sideband (SSB) signals for the extracted regions by performing a tangent inverse operation on the ratio of their real and imaginary parts.

The obtained phase is now constrained to the principle values, i.e., $\pi$ to $\pi$. Further, an unwrap operation is performed to the phase by adding multiples of $\pm 2\pi$ whenever a jump in phase is greater than $\pi$, so as to bring it to a magnitude smaller than $\pi$ (step 306A). This unwrapped phase is linear with a few breakpoints or knots in the linear trend, corresponding to the boundaries of echo arising from each tissue interface along the ultrasound scan line. Identification of the locations of these breakpoints is performed using a unidirectional signal f(t) derived from the first-time derivative of the unwrapped phase waveforms (step 308A). More specifically, the f(t) signal is obtained by subtracting the first-time derivative of the unwrapped phase with its mean and then performing a modulus operation (step 310A). This procedure delineates various echoes from different tissue interfaces in the extracted regions of the proximal wall and the distal wall. Further, the locations of interest, such as the locations corresponding to the lumen-intima and media-adventitia, are identified.

The interfaces of lumen-intima and media-adventitia are located from the pool of all the identified echo boundaries of the extracted region, as follows. Envelopes are first constructed for the proximal and distal wall region extracts using a suitable method (304B). One method is to use the SSB signals of the regions, where the envelope can be estimated as the magnitude of the complex-valued elements. An over smoothened version of this envelope is obtained, and its peak is identified (step 306B). The location of the obtained peak ($L_P$) for the respective regions represent the location at which maximum energy of the extracted regions are concentrated (step 308B). Further, the two strong echoes that are present to either side of this peak are the echoes formed due to lumen-intima and media-adventitia interfaces (step 310B). In the case of a proximal wall, the echo on the right side of $L_P$ is identified as the echo originated from the intima layer, and the echo on the left side of $L_P$ as the echo originated from the adventitia layer. Similarly, for distal wall region, the echo immediately to the left of the $L_P$ is identified as the echo originated from the intima layer, and echo on the right side of $L_P$ as the echo originated from the adventitia layer.

Amongst all the echo boundaries previously identified for the proximal wall region, the leading boundary location of the intima echo is designated as the lumen-intima interface ($LI_{PROX}$), and the trailing boundary of the adventitia echo is designated as the media-adventitia interface ($MA_{PROX}$) Also, amongst all the echo boundaries previously identified for the distal wall region, the leading boundary location of the intima echo is designated as the lumen-intima interface ($LI_{DIS}$), and the leading boundary of the adventitia echo is designated as the media-adventitia interface ($MA_{DIS}$). These interfaces are identified for the $F^{th}$ and $(F-1)^{th}$ frames (step 318). The difference in the $LI_{PROX}$ from the two frames and in the $MA_{PROX}$ from the two frames are averaged to yield the proximal wall shift. A similar approach is adopted to produce the distal wall shift (step 320).

Another robust approach for wall shift estimation is to find the ΔΦ waveform for the combined intima and adventitia echoes that were identified in the $F^{th}$ and $(F-1)^{th}$ frames for respective wall regions. Further, the shift in locations of the proximal and distal wall echoes in units of time (measured as difference in time of flight of echoes in $F^{th}$ and $(F-1)^{th}$ frames) are estimated by translating the average of values in the ΔΦ waveform using the expression; shift (in seconds)=(average of elements in ΔΦ)/(2π frequency of transducer).

These shifts corresponding to the $F^{th}$ frame are added to the previously accumulated shifts till $(F-1)^{th}$ (step 324A and step 324B). If the tracing has just started, this previously accumulated shift is initialised with zero. This procedure, therefore, traces the shifts in the echoes continuously with every new incoming frame. The exact locations of the wall in the current frame are computed by adding the current accumulated shifts with the initially identified wall locations. These exact locations assist in shifting of the window centre that extracts the proximal and distal wall regions in the consecutive frames (step 328A and step 328B). The difference between the traces of accumulated shifts in the proximal and distal walls provide distension trace. Likewise, the difference between the traces of exact locations of the proximal and distal walls in the frame produces the diameter waveform. The proximal wall and distal wall locations are buffered for every N sufficient samples (step 330), and the mutual motion pattern between them is quantified (step 332). This motion pattern is inspected by comparing the physiological characteristic motion pattern of the arterial walls (step 334). The tracing of the walls is continued until the inspected motion concurs with the expected characteristic motion (step 336). Otherwise, the locations of the walls are again freshly identified (step 338).

Figure 4:
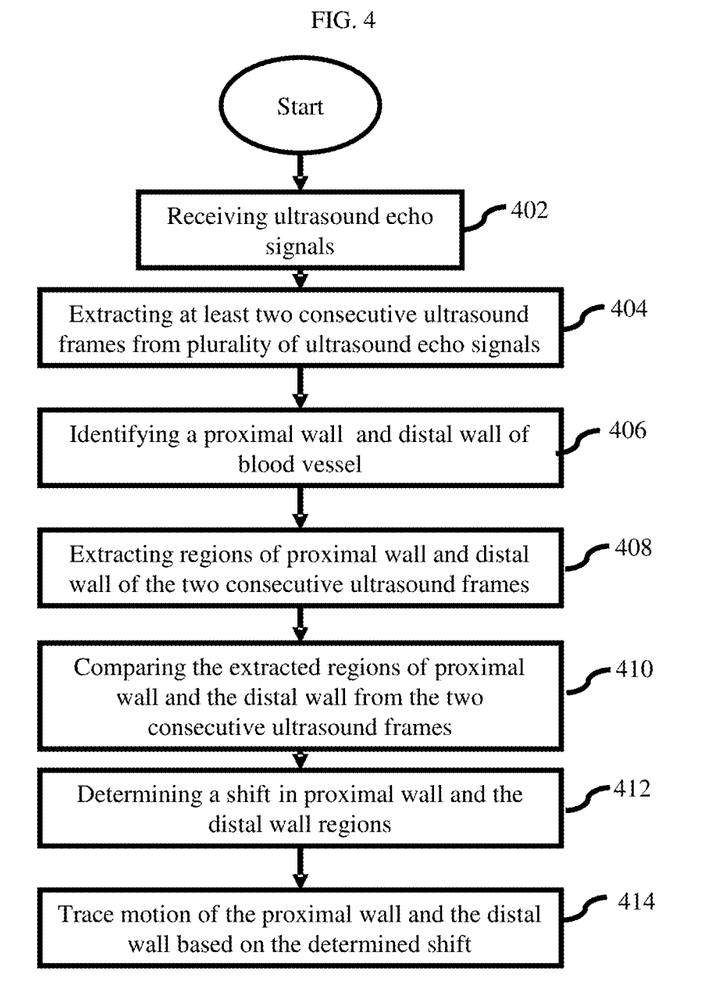
FIG. 4 is a flow diagram, illustrating the primary stages of the method for tracing motion of the boundaries of the vessel in the body, in accordance with various embodiments of the present disclosure.

FIG. 4 is a flow diagram (400), illustrating the method of tracing the motion of the blood vessel in the human body, according to an embodiment as disclosed herein.

As seen in FIG. 4, At 402, the method comprises receiving ultrasound echo signals from the transducer by the vascular-dynamics-monitoring device (100) from different location of the blood vessel.

At 404, the method comprises continuously extracting, by the vascular-dynamics-monitoring device (100), at least two consecutive ultrasound frames from the ultrasound echo signals.

At (406), the method comprises identifying, by the vascular-dynamics-monitoring device (100), the proximal wall and a distal wall of the blood vessel from the at least two consecutive ultrasound frames from the plurality of ultrasound signals.

At (408), the method includes dynamically extracting, by the vascular-dynamics-monitoring device (100), at least one echo region of the proximal wall and the distal wall of the blood vessels.

At (410), the at least one echo region from each of the at least two consecutive ultrasound frames are compared to determine at least one delay waveform between the each of the regions or first time-derivative of unwrapped analytic phase waveforms of the each of the proximal wall echo region and the distal wall region. In an embodiment, samples of the each echo regions of the proximal wall and the distal walls are compared to determine an alignment dissimilarity between the echo regions. The two-dimensional alignment error matrix is generated based on the alignment dissimilarity between the echo regions. The two-dimensional error matrix is translated to accumulated distance matrix. Further the local minimum accumulated errors and global minimum accumulated errors are determined from the accumulated distance matrix. Finally, the delay waveform is generated based on the determined local minimum accumulated errors and the global minimum accumulated errors. In another embodiment, samples of the each echo regions of the proximal wall and the distal walls are used to determine a quadrature phase counterpart corresponding to each of the at least one echo region by applying Hilbert transform on the each of the at least two ultrasound frames and generate a single sideband (SSB) signal corresponding to each of the at least one echo region. A tangent inverse operation was performed on the SSB signal corresponding to each of the at least one echo region by which the unwrapped phase waveforms were constructed and, differentiated with respect to time once.

At (412), the vascular-dynamics-monitoring device (100) determines the shift of the at least one echo region on each of the proximal wall and the distal wall based on the comparison.

At (414), the vascular-dynamics-monitoring device (100), traces the motion of the proximal wall and the distal wall based on the continuously determined motion shift of the at least one echo region on each of the proximal wall and the distal wall.

Figure 5:
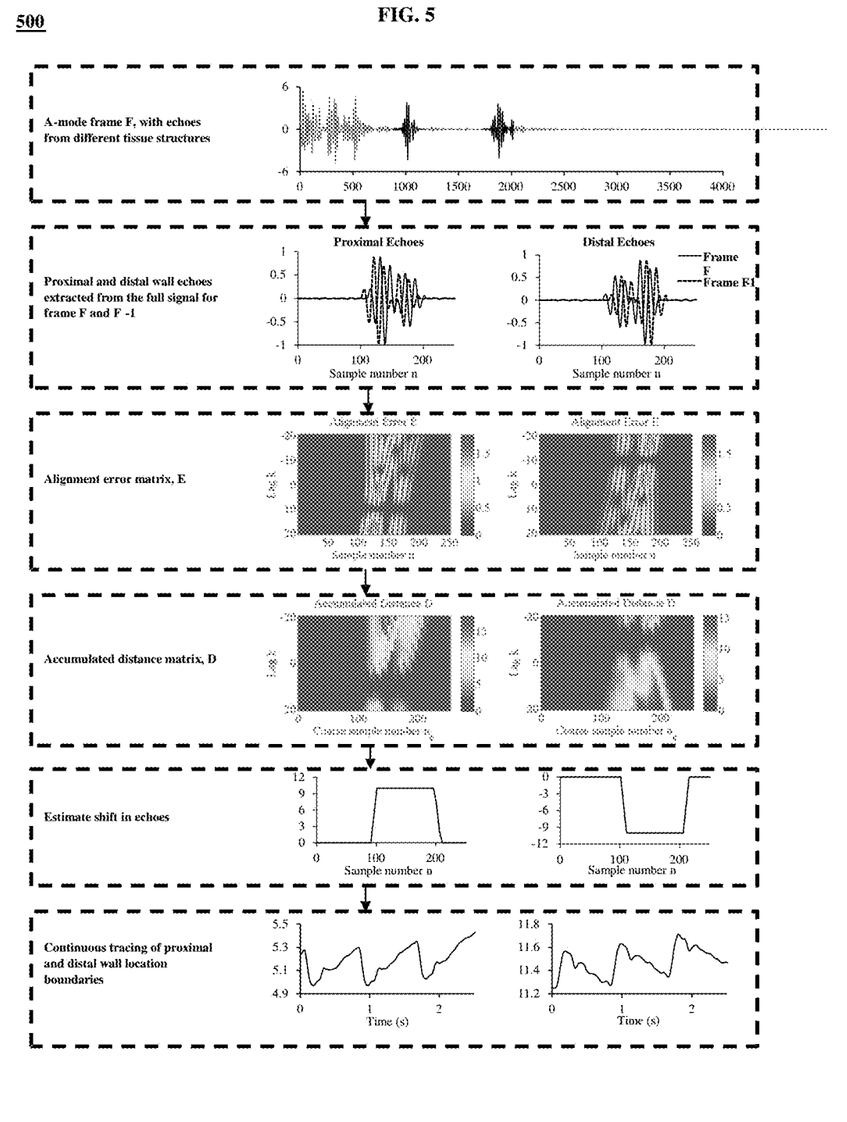
FIG. 5 is a set of intermediate-stage signal graph illustrating the time domain method to trace motion of boundaries of a vessel in the human body using the vascular-dynamics-monitoring device, in accordance with various embodiments of the present disclosure.

FIG. 5 is a set of intermediate-stage signal graphs 500 illustrating the time domain method to trace motion of boundaries of a vessel in a body using the vascular-dynamics-monitoring device 100, in accordance with various embodiments of the present disclosure. Approximate locations of vessel boundaries act as the initial locations of the proximal and distal walls. As shown in FIG. 5, two windows of sufficient and equal size (dynamically allocated) are placed around the echoes originated from the proximal and distal wall boundaries. The centre portion of the said windows are placed, however not constrained, at the previously identified boundary locations. Such extracted subsets from $F^{th}$ and $(F-1)^{th}$ frames are then analysed.

Ultrasound frames are continuously collected from the echo regions and stored in a buffer. Two consecutive frames, the current frame F and its previous frame (F−1) are used at a time. Typically, both $F^{th}$ and $(F-1)^{th}$ frame have an equal number of samples (N), else are made equal. From these the proximal and the distal wall subsets are extracted. Then the alignment dissimilarity between these frames' subsets is measured by generating an error matrix E. Since two consecutive frames are used, the error matrix will be a two-dimensional matrix. The same operation can be performed with any desired number of successive frames, which would result in an error matrix with the corresponding dimensionality Once the error matrix E(k,n) is derived, it is translated to an 'accumulated error matrix' D(k,n) as a representation of the cumulative errors while traversing across the length of the frame via a various lag path as shown in FIG. 5. This form of generating accumulated error matrix process iteratively adds the minimum of the adjoining elements presents one column apart. Now the 'local minimum accumulated errors' are computed by traversing in the reverse direction, that is from $N^{th}$ column to $1^{st}$ column of D(k,n).

These accumulated error matrices are used to derive the delay waveform L(n), in the form of lags that best align the consecutive frame signals, for the proximal and distal wall echo regions. Once the delay waveforms are generated as shown in FIG. 5, for both the proximal and distal wall region, the extrema of their respective delay waveforms are identified and labelled. Extrema of the delay waveform represent the shifts of the proximal and distal subset echoes from $(F-1)^{th}$ to $F^{th}$ frame. The shifts of proximal and distal walls corresponding to the $F^{th}$ frame are added to their accumulated shifts (resultant shift till $(F-1)^{th}$ frame). If the tracing has just started, this previously accumulated shift can be set to a predefined value (typically initialized with zero). This procedure, therefore, continuously traces the shifts in the echoes of the selected region with every new incoming frame. The exact locations of the vessel wall boundaries in the current frame are computed by adding the current accumulated shifts with the initially identified wall locations. These exact locations further assist in shifting of the window centre that extracts the proximal and distal wall regions in the consecutive frames. The proximal wall and distal wall locations are buffered for sufficient samples, and the mutual motion pattern between them is quantified, as shown in FIG. 5. This motion pattern is inspected by comparing the expected physiological characteristic motion pattern of the arterial walls. The tracing of the walls is continued until the inspected motion concurs with the expected characteristic motion; otherwise, the locations of the walls are again freshly identified.

Figure 6:
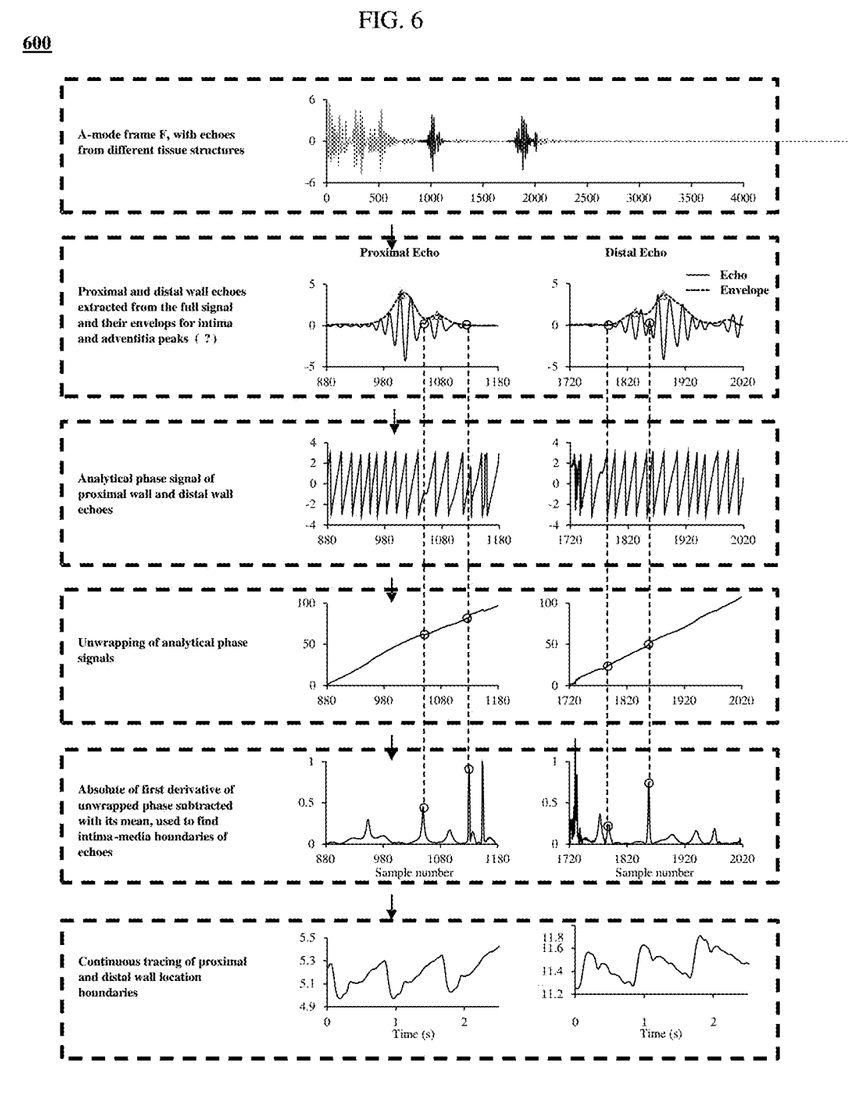
FIG. 6 is a set of intermediate-stage signal graph illustrates the frequency domain method to trace motion of boundaries of a vessel in a body using the vascular-dynamics-monitoring device, in accordance with various embodiments of the present disclosure.

FIG. 6 is a set of intermediate-stage signal graphs 600 illustrates the frequency domain method to trace motion of boundaries of a vessel in a body using the vascular-dynamics-monitoring device 100, in accordance with various embodiments of the present disclosure.

The locations of vessel wall boundaries (proximal and distal wall locations) identified via a suitable manual or automated method act as the initial reference locations to trace the wall dynamics and motion (or vibrations) of vessel walls. Initially, a window with the dynamically allocated size is used to extract the proximal and distal wall echo regions constituting a sufficient number of samples (step 310 and step 302). Hilbert transform operation is applied on these proximal and distal wall echo regions of the $F^{th}$ and $(F-1)^{th}$ frame which yields their respective quadrature-phase counterpart. By adding the regions from the original frames (F and (F−1)) with their quadrature versions, G and (G−1), respectively single-sideband (SSB) signals are generated as shown in FIG. 6.

The obtained phase is now constrained to the principle values, i.e., $\pi$ to $\pi$. Further, an unwrap operation is performed to the phase by adding multiples of $\pm 2\pi$ whenever a jump in phase is greater than $\pi$, so as to bring it to a magnitude smaller than $\pi$. This unwrapped phase is linear with a few breakpoints or knots in the linear trend, corresponding to the boundaries of echo arising from each tissue interface along the ultrasound scan line as shown in FIG. 6. Identification of the locations of these breakpoints is performed using a unidirectional signal derived from the first-time derivative of the unwrapped phase waveforms. More specifically, the unidirectional signal is obtained by subtracting the first-time derivative of the unwrapped phase with its mean and then performing a modulus operation This procedure delineates various echoes from different tissue interfaces in the extracted regions of the proximal wall and the distal wall. Further, the locations of interest, such as the locations corresponding to the lumen-intima and media-adventitia, are identified as shown in FIG. 6.

The interfaces of lumen-intima and media-adventitia are located from the pool of all the identified echo boundaries of the extracted region, as follows. Envelopes are first constructed for the proximal and distal wall region extracts using a suitable method. One method is to use the SSB signals of the regions, where the envelope can be estimated as the magnitude of the complex-valued elements. An over smoothened version of this envelope is obtained, and its peak is identified. The location of the obtained peak (LP) for the respective regions represent the location at which maximum energy of the extracted regions are concentrated. Further, the two strong echoes that are present to either side of this peak are the echoes formed due to lumen-intima and media-adventitia interfaces. In the case of a proximal wall, the echo on the right side of LP is identified as the echo originated from the intima layer, and the echo on the left side of LP as the echo originated from the adventitia layer. Similarly, for distal wall region, the echo immediately to the left of the LP is identified as the echo originated from the intima layer, and echo on the right side of LP as the echo originated from the adventitia layer.

Amongst all the echo boundaries previously identified for the proximal wall region, the leading boundary location of the intima echo is designated as the lumen-intima interface ($LI_{PROX}$), and the trailing boundary of the adventitia echo is designated as the media-adventitia interface ($MA_{PROX}$) Also, amongst all the echo boundaries previously identified for the distal wall region, the leading boundary location of the intima echo is designated as the lumen-intima interface ($LI_{DIS}$), and the leading boundary of the adventitia echo is designated as the media-adventitia interface ($MA_{DIS}$). These interfaces are identified for the Fth and (F−1)th frames. The difference in the $LI_{PROX}$ from the two frames and in the $MA_{PROX}$ from the two frames are averaged to yield the proximal wall shift. A similar approach is adopted to produce the distal wall shift, as shown in FIG. 6.

Shifts corresponding to the Fth frame are added to the previously accumulated shifts till (F−1)th frame. If the tracing has just started, this previously accumulated shift is initialised with zero. This procedure, therefore, traces the shifts in the echoes continuously with every new incoming frame. The exact locations of the wall in the current frame are computed by adding the current accumulated shifts with the initially identified wall locations. These exact locations assist in shifting of the window centre that extracts the proximal and distal wall regions in the consecutive frames. The difference between the traces of accumulated shifts in the proximal and distal walls provide distension trace. Likewise, the difference between the traces of exact locations of the proximal and distal walls in the frame produces the diameter waveform. The proximal wall and distal wall locations are buffered for every N sufficient samples, and the mutual motion pattern between them is quantified. This motion pattern is inspected by comparing the physiological characteristic motion pattern of the arterial walls. The tracing of the walls is continued until the inspected motion concurs with the expected characteristic motion as shown in FIG. 6. Otherwise, the locations of the walls are again freshly identified.

The foregoing descriptions of specific embodiments of the present technology have been presented for purposes of illustration and description. They are not intended to be exhaustive or to limit the present technology to the precise forms disclosed, and obviously many modifications and variations are possible in light of the above teaching. The embodiments were chosen and described in order to best explain the principles of the present technology and its practical application, to thereby enable others skilled in the art to best utilize the present technology and various embodiments with various modifications as are suited to the particular use contemplated. It is understood that various omissions and substitutions of equivalents are contemplated as circumstance may suggest or render expedient, but such are intended to cover the application or implementation without departing from the spirit or scope of the claims of the present technology.

While several possible embodiments of the invention have been described above and illustrated in some cases, it should be interpreted and understood as to have been presented only by way of illustration and example, but not by limitation. Thus, the breadth and scope of a preferred embodiment should not be limited by any of the above-described exemplary embodiments.

We claim:

1. A method for tracing motion of blood vessel boundaries in a human body, the method comprising:
   receiving, by an vascular-dynamics-monitoring device (100), a plurality of ultrasound signals from the blood vessel;
   continuously extracting, by the vascular-dynamics-monitoring device (100), at least two consecutive ultrasound frames from the plurality of ultrasound signals;
   identifying, by the vascular-dynamics-monitoring device (100), a proximal wall and a distal wall of the blood vessel from the at least two consecutive ultrasound frames from the plurality of ultrasound signals;
   dynamically extracting, by the vascular-dynamics-monitoring device (100), at least one echo region of the proximal wall and the distal wall of the blood vessels;
   comparing, by the vascular-dynamics-monitoring device (100), the at least one echo region from each of the at least two consecutive ultrasound frames a first time-derivative of unwrapped analytic phase waveforms of the each of the proximal wall echo region and the distal wall region wherein the first time-derivative of unwrapped analytic phase waveforms comprises:
      determining a quadrature phase counterpart corresponding to each of the at least one echo region of each of the at least two ultrasound frames by applying Hilbert transform on each of the at least one echo region of the each of the at least two ultrasound frames;
      generating a single sideband (SSB) signal corresponding to each of the at least one echo region of each of the at least two ultrasound frames by adding the each of the echo regions to the corresponding quadrature phase counterpart;
      constructing continuous phase waveforms of each of the echo regions by performing a tangent inverse operation on the SSB signal corresponding to each of the at least two ultrasound frames; and
      constructing the unwrapped phase waveforms by performing a time-domain unwrapping operation, differentiating the unwrapped phase waveforms of each of the at least one echo region of each of the proximal wall and the distal wall with respect to time once;
   determining, by the vascular-dynamics-monitoring device (100), a shift of the at least one echo region on each of the proximal wall and the distal wall based on the first time-derivative of the unwrapped analytic phase waveforms; and
   tracing, by the vascular-dynamics-monitoring device (100), the motion of the proximal wall and the distal wall based on the continuously determined motion shift of the at least one echo region on each of the proximal wall and the distal wall.

2. The method as claimed in claim 1, further comprising continuing tracing by the vascular-dynamics-monitoring device (100) the motion of the proximal wall and the distal wall until the tracing concurs with an expected motion of the proximal wall and the distal wall.

3. The method as claimed in claim 1, wherein the ultrasound frame is a digitized data frame of the ultrasound signal with a finite number of samples.

4. The method as claimed in claim 1, wherein the proximal wall and the distal wall of the blood vessel move in opposite directions.

5. The method as claimed in claim 1, wherein dynamically extracting the at least one echo region on each of the proximal wall and the distal wall comprises placing at least two windows with dynamically allocated sizes around each of the plurality of ultrasound signals received from the identified proximal wall and the identified distal wall.

6. The method as claimed in claim 1, wherein comparing the at least one echo region of each of the proximal wall and the distal wall of each of the at least two consecutive ultrasound frames is to determine at least one delay waveform between the each of the regions or the first time-derivative of unwrapped analytic phase waveforms of the each of the proximal wall echo region and the distal wall region.

7. The method as claimed in claim 6, wherein determining the delay waveform between each of the proximal wall echo region and the distal wall region comprises:
   comparing samples of the each echo regions of the proximal wall and the distal wall to determine an alignment dissimilarity between the echo regions;
   generating a two-dimensional alignment error matrix based on the alignment dissimilarity between the echo regions;
   translating the two-dimensional error matrix to an accumulated distance matrix;
   determining local minimum accumulated errors and global minimum accumulated errors from the accumulated distance matrix; and
   generating the delay waveform based on the determined local minimum accumulated errors and the global minimum accumulated errors.

8. The method as claimed in claim 1, wherein determining the shift comprises determining at least one extremum of a delay waveform or at least two extrema of interest of the first time-derivative of the unwrapped analytic phase waveforms, where the at least one extremum of the delay waveform or an average shift in the at least two extrema of interest of the first time-derivative of the unwrapped analytic phase waveforms.

9. The method as claimed in claim 1, wherein the ultrasound frames comprise an equal number of samples.

10. The method as claimed in claim 1, wherein the ultrasound frames comprise an unequal number of samples.

11. A vascular-dynamics-monitoring device (100) for tracing motion of a blood vessel in a human body, the vascular-dynamics-monitoring device (100) comprising:
   a memory (102) for storing ultrasound frames;
   a signal transceiver (104) configured for receiving a plurality of ultrasound echo signals from an ultrasound transducer (110), wherein the plurality of ultrasound echo signals are transmitted to the ultrasound transducer (110) from the blood vessel;
   a sample extractor (106) communicatively coupled to the signal transceiver (104) and the memory (102), configured for:
      continuously extracting at least two consecutive ultrasound frames from the plurality of ultrasound echo signals received from at least one echo region;

dynamically extracting at least one echo region from each of the at least two ultrasound frames, and storing the at least two consecutive ultrasound frames and the at least one echo region in the memory (110);

a controller (108) communicatively connected to the sample extractor (106), the signal transceiver (104) and the memory (102), configured to:

compare the at least one echo region of each of a proximal wall and a distal wall of each of the at least two consecutive ultrasound frames to determine a first time-derivative of unwrapped analytic phase waveforms of the each of the proximal wall echo region and the distal wall region, wherein the first time-derivative of unwrapped analytic phase waveforms:

determining a quadrature phase counterpart corresponding to each of the at least one echo region of each of the at least two ultrasound frames by applying Hilbert transform on the at least one echo region of each of the at least two ultrasound frames;

generating a single sideband (SSB) signal corresponding to each of the at least one echo region of each of the at least two ultrasound frames by adding the each of the echo regions to the corresponding quadrature phase counterpart;

constructing continuous phase waveforms of each of the echo regions by performing a tangent inverse operation on the SSB signal corresponding to each of the at least two ultrasound frames; and constructing the unwrapped phase waveforms by performing a time-domain unwrapping operation, differentiating the unwrapped phase waveforms of each of the at least one echo region of each of the proximal wall and the distal wall with respect to time once;

determine a shift of the at least one echo region on each of the proximal wall and the distal wall based on the first time-derivative of the unwrapped analytic phase waveforms; and trace the motion of the proximal wall and the distal wall based on the continuously determined motion shift of the at least one echo region on each of the proximal wall and the distal wall.

12. The vascular-dynamics-monitoring device (100) as claimed in claim 11, further comprising continuing tracing of the proximal wall and the distal wall until the tracing concurs with an expected motion of the proximal wall and the distal wall.

13. The vascular-dynamics-monitoring device (100) as claimed in claim 11, wherein an ultrasound frame is a digitized data frame of the ultrasound echo signal with a finite number of samples.

14. The vascular-dynamics-monitoring device (100) as claimed in claim 11, wherein the proximal wall and the distal wall of the blood vessel of the user move in opposite directions.

15. The vascular-dynamics-monitoring device (100) as claimed in claim 11, wherein dynamically identifying at least one echo region on each of the proximal wall and the distal wall comprises placing at least two windows with dynamically allocated sizes around each of the plurality of ultrasound signals received from the identified proximal wall and the identified distal wall.

16. The vascular-dynamics-monitoring device (100) as claimed in claim 11, wherein comparing the at least one echo region of each of the proximal wall and the distal wall of each of the at least two consecutive ultrasound frames is to determine at least one delay waveform between the each of the regions or the first time-derivative of unwrapped analytic phase waveforms of the each of the proximal wall echo region and the distal wall region.

17. The vascular-dynamics-monitoring device (100) as claimed in claim 16, wherein determining the delay waveform between the corresponding echo regions of the at least two consecutive ultrasound frames comprises:

comparing samples of the echo regions to determine an alignment dissimilarity between the echo regions;

generating a two-dimensional alignment error matrix based on the alignment dissimilarity between the echo regions;

translating the two-dimensional error matrix to an accumulated distance matrix;

determining local minimum accumulated errors and global minimum accumulated errors from the accumulated distance matrix; and generating the delay waveform based on the determined local minimum accumulated errors and the global minimum accumulated errors.

18. The vascular-dynamics-monitoring device (100) as claimed in claim 11, wherein determining the shift comprises determining at least one extremum of a delay waveform or at least two extrema of interest of the first time-derivative of the unwrapped analytic phase waveforms, where the at least one extremum of the delay waveform or an average shift in the at least two extrema of interest of the first time-derivative of the unwrapped analytic phase waveforms.

19. The vascular-dynamics-monitoring device (100) as claimed in claim 11, wherein the echo regions comprise an equal number of samples.

20. The vascular-dynamics-monitoring device (100) as claimed in claim 11, wherein the echo regions comprise an unequal number of samples.

* * * * *